(12) United States Patent
Grascha et al.

(10) Patent No.: US 8,580,861 B2
(45) Date of Patent: Nov. 12, 2013

(54) CHEMICAL COMPOSITION FOR SKIN CARE FORMULATIONS

(75) Inventors: Pierre Bruno Grascha, Cormontreuil (FR); Mylene Battut, La Norville (FR)

(73) Assignee: Pibed Limited, Belper (GB)

( * ) Notice: Subject to any disclaimer, the term of this patent is extended or adjusted under 35 U.S.C. 154(b) by 640 days.

(21) Appl. No.: 12/222,803

(22) Filed: Aug. 15, 2008

(65) Prior Publication Data

US 2010/0040702 A1 Feb. 18, 2010

(51) Int. Cl.
| | |
|---|---|
| A61K 31/045 | (2006.01) |
| A61K 31/194 | (2006.01) |
| A61K 31/131 | (2006.01) |
| A61K 33/04 | (2006.01) |
| A01N 31/04 | (2006.01) |
| A01N 37/06 | (2006.01) |
| A01N 59/02 | (2006.01) |

(52) U.S. Cl.
USPC ............ 514/730; 514/784; 514/740; 424/710

(58) Field of Classification Search
None
See application file for complete search history.

(56) References Cited

U.S. PATENT DOCUMENTS

| | | | | |
|---|---|---|---|---|
| 4,485,091 | A | * 11/1984 | Fitton | 424/62 |
| 4,921,694 | A | 5/1990 | Hoppe et al. | |
| 5,098,694 | A | 3/1992 | Komp et al. | |
| 5,318,726 | A | * 6/1994 | Rossmaier et al. | 510/361 |
| 5,460,802 | A | 10/1995 | Asami et al. | |
| 2004/0105831 | A1 | * 6/2004 | Frantz et al. | 424/70.12 |
| 2004/0228888 | A1 | 11/2004 | Kohlhase et al. | |
| 2006/0008434 | A1 | * 1/2006 | Knopf et al. | 424/65 |
| 2007/0265352 | A1 | 11/2007 | Roeding et al. | |
| 2009/0325857 | A1 | * 12/2009 | Beumer et al. | 514/2 |

FOREIGN PATENT DOCUMENTS

| | | |
|---|---|---|
| EP | 0 420 630 | 4/1991 |
| GB | 2 345 636 | 7/2000 |
| WO | WO 91/09106 * | 6/1991 ............ A61K 7/00 |
| WO | 02/19981 | 3/2002 |
| WO | 2006/096239 | 9/2006 |

OTHER PUBLICATIONS

Inoue et al. (FEMS Microbiology Letters 2004, 237, 325-331).*
Kubo et al. (Bioorganic & Medicinal Chemistry 1995, 3, 873-880).*
Brehm-Stecher et al. "Sensitization of *Staphylococcus aureus* and *Escherichia coli* to antibiotics by the sesquiterpenoids nerolidol, farnesol, bisabolol, and apritone." Antimicrobial Agents and Chemotherapy. American Society for Microbiology. vol. 47, No. 10, pp. 3357-3360. Oct. 1, 2003.
Liu et al. "Inhibition of protease production of various bacteria by ammonium salts: its effect on toxin production and virulence." Journal of Bacteriology. vol. 99, No. 2, pp. 406-413. Aug. 1969.
Comes et al. "Addition of fumaric acid and sodium benzoate as an alternative method to achieve a 5-log reduction of *Escherichia coli* 0157:H7 populations in apple cider." Journal of Food Protection. International Association for Food Protection. vol. 65, No. 3, pp. 476-483. Mar. 1, 2002.
Lee et al. "Antifungal effect of eugenol and nerolidol against *Microsporum gypseum* in a guinea pig model." Medicinal & Aromatic Plants Abstracts. Scientific Publishers. vol. 29, No. 6, p. 187. Dec. 1, 2007.
Inoue et al. "The antibacterial effects of terpene alcohols on *Staphylococcus aureus* and their mode of action." FEMS Microbiology Letters. vol. 237, pp. 325-331. Jul. 8, 2004.
Siegert, Wolfgang. "Can new biodegradable complexing agents replace tetrasodium edta to boost preservatives?" SOFW Journal. No. 134, pp. 22-26. Jan. 2008.

* cited by examiner

*Primary Examiner* — James H Alstrum Acevedo
*Assistant Examiner* — Jessica Kassa
(74) *Attorney, Agent, or Firm* — Dowell & Dowell, P.C.

(57) ABSTRACT

The present invention provides preservative compositions suitable for replacing, partially or in totality, conventional preservatives in skin care and hygiene cosmetic or pharmaceutical products. The preservative formulations include an organic carboxylic acid present in a concentration from about 0.01 to about 30 wt./wt. % of the formulation, an alcohol present in a concentration from about 0.01 to about 60 wt./wt. % of the formulation. The formulations include an inorganic salt present in a concentration from about 0.01 to about 80 wt./wt. % of the formulation, and a chelating agent present in a concentration from about 0.01 to about 20 wt./wt. % of the formulation.

11 Claims, 4 Drawing Sheets

CHEMICAL COMPOSITION FOR SKIN CARE FORMULATIONS

FIELD OF THE INVENTION

The present invention relates to a chemical composition designed to protect cosmetic or pharmaceutical water-based products from microbial degradation, with or without using conventional preservatives.

BACKGROUND TO THE INVENTION

The term "preservative" is generally defined as an industry-recognized ingredient the purpose of which is to prevent microbial growth in consumer products such as a cosmetics and food. Some preservatives (formaldehyde releasers, isothiazolinones . . . ) are known to cause a host of skin irritations, such as dryness, redness and even breakouts. The only goal of preservatives is to extend the life of a product beyond what it would be naturally in the absence of the preservative. As mentioned, the most significant concern with respect to preservatives in personal skin products, cosmetics, soaps etc. would be skin irritations that can vary from mild to very severe. Preservatives can cause many skin disorders and allergies from eczema to rosacea to blemishes.

Some natural or synthetic materials are not regulated as preservatives, yet when used for their beneficial effect on the skin, may coincidentally have a positive effect on the total preservative requirement of the formulation. In view of increasing pressure from consumers and cosmetic regulation bodies alike, and because of bad press concerning the presence and use of more and more chemical preservatives (especially formaldehyde releasers and parabens), it would be advantageous to formulate preservative-free products that do not rely on, or incorporate presently regulated as preservatives.

It would therefore be advantageous to provide preservative-free formulations for protecting cosmetic or pharmaceutical water-based products from microbial degradation.

SUMMARY OF THE INVENTION

The inventors have discovered preservative compositions using a natural biochemical process, involving alternative molecular compounds than found in known commercial preservatives.

The present invention provides preservative compositions suitable for replacing, partially or in totality, conventional preservatives in skin care and hygiene cosmetic or pharmaceutical products.

The present chemical compositions have no known potential toxicity or ecotoxicity, are not regulated as preservatives, have nothing in common with existing preservatives on the market, and have demonstrated efficacy for bacteriostatic and fungistatic properties.

The present invention provides a preservative formulation for skin care and hygiene products, comprising constituents including:

a) at least one organic carboxylic acid that is maleic acid present in a concentration from about 0.01 to about 30 wt./wt. % of the formulation;

b) at least one alcohol that is a phenyl alcohol present in a concentration from about 0.01 to about 60 wt./wt. % of the formulation;

c) ammoniumsulphate present in a concentration from about 0.01 to about 80 wt./wt. % of the formulation; and d) at least one chelating agent that is a sodium salt of iminosuccinic acid present in a concentration from about 0.01 to about 20 wt./wt. % of the formulation.

The present invention also provides a preservative formulation for skin care products, comprising:

maleic acid present in a concentration from about 0.01 to about 30 wt./wt. % of the formulation;

phenyl hexanol present in a concentration from about 0.01 to about 60 wt./wt. % of the formulation;

ammonium sulphate present in a concentration from about 0.01 to about 80 wt./wt. % of the formulation; and a chelating agent, sodium iminodisuccinate, present in a concentration from about 0.01 to about 20 wt./wt. % of the formulation.

The present invention also provides a preservative formulation for surfactant-containing hygiene products or emulsions, gels and lotions for skin care products, comprising constituents including:

a) maleic acid present in a concentration from about 0.01 to about 30 wt./wt. % of the formulation;

b) at least one alcohol selected from a group of alcohols consisting of non-terpenic aromatic alcohols present in a concentration from about 0.01 to about 60 wt./wt. % of the formulation;

c) ammonium sulphate present in a concentration from about 0.01 to about 80 wt./wt. % of the formulation; and d) at least one chelating agent present in a concentration from about 0.01 to about 20 wt./wt. % of the formulation; and wherein e) the preservative formulation is incorporated into the surfactant-containing hygiene products or emulsions, gels and lotions for skin care, in a concentration range from about 0.1 to about 80 wt./wt. % of the products.

The present invention also provides a preservative formulation for skin care and hygiene products, comprising constituents including:

a) maleic acid present in a concentration from about 0.01 to about 30 wt./wt. % of the formulation;

b) at least one alcohol selected from a group of alcohols consisting of non-terpenic aromatic alcohols present in a concentration from about 0.01 to about 60 wt./wt. % of the formulation;

c) ammonium sulphate present in a concentration from about 0.01 to about 80 wt./wt. % of the formulation;

d) at least one chelating agent present in a concentration from about 0.01 to about 20 wt./wt. % of the formulation; and wherein e) the preservation formulation of constituents a), b), c), and) is incorporated into the skin care and hygiene products in a concentration range from about 0.1 to about 10 wt./wt. % of the product.

BRIEF DESCRIPTION OF THE DRAWINGS

Preferred embodiments of the invention will now be described, by way of example only, with reference to the drawings, in which.

DETAILED DESCRIPTION OF THE INVENTION

Figure 1:
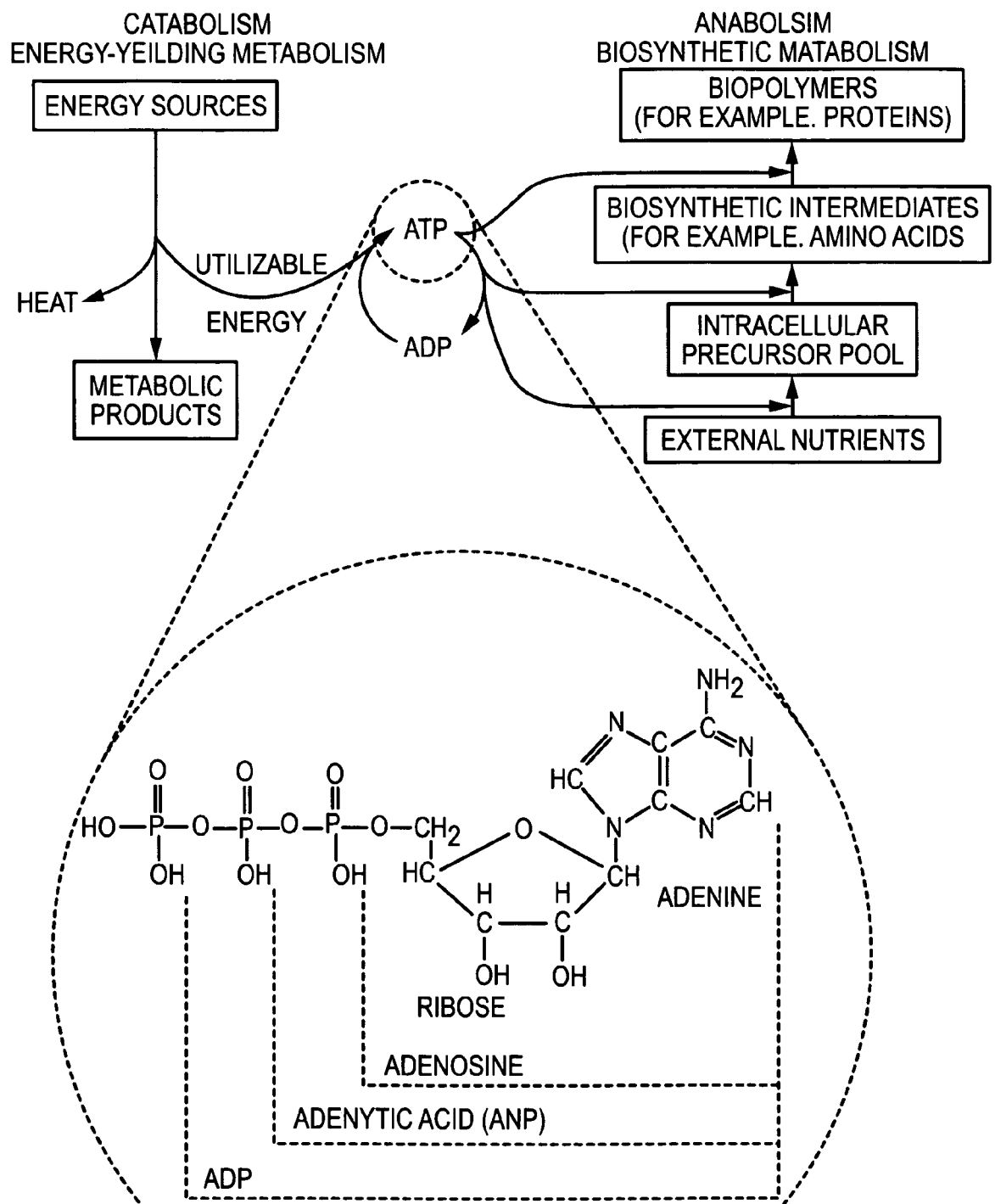
FIG. 1 is a diagrammatic representation of the relationship between catabolism and anabolism.

Generally speaking, the embodiments described herein are directed to chemical formulations as preservatives comprised of alternative molecular compounds than found in conventional preservative formulations. As required, embodiments of the present invention are disclosed herein. However, the disclosed embodiments are merely exemplary, and it should be understood that the invention may be embodied in many various and alternative forms.

The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, chemical formulations as preservatives comprised of alternative molecular compounds than in known preservative formulations are disclosed.

As used herein, the terms "about", and "approximately" when used in conjunction with ranges of dimensions, concentrations, temperatures or other physical properties or characteristics is meant to cover slight variations that may exist in the upper and lower limits of the ranges of properties/characteristics.

Embodiments of the preservative composition disclosed herein include at least one organic carboxylic acid in a concentration from about 0.01 to about 30 wt./wt. % of the formulation, at least one alcohol in a concentration from about 0.01 to about 60 wt./wt. % of the formulation, at least one inorganic salt in a concentration from about 0.01 to about 80 wt./wt. % of the formulation, and at least one chelating agent present in a concentration from about 0.01 to about 20 wt./wt. % of the blend.

The organic carboxylic acid may be any one of butenedioic (succinic) acid, or cis(maleic)- or trans(fumaric)-isomers of butenedioic acid, and any mixtures thereof. A preferred organic carboxylic acid is maleic acid.

The alcohol may be any one of $C_2$ to $C_{22}$-alkyl alcohols, aryl (aromatic) alcohols, aromatic alcohols terpenic alcohols, any of their isomers, and mixtures thereof. Preferred alcohols are phenyl alcohol and/or sesquiterpenic alcohol or combinations thereof. Even more preferred alcohols are phenyl hexanol and/or nerolidol (3,7,11-trimethyl1,6,10-dodecatrien-3-ol), and any mixture thereof.

The inorganic salt may be any one of salts of strong acids and nitrogen-containing base, and any mixtures thereof. A preferred inorganic salt is ammonium sulphate.

The chelating agent may be any one of biodegradable chelating agents such as gluconic acid, its sodium salts, iminodisuccinic acid, its sodium salts, and any mixtures thereof. The biodegradable chelating agent is preferably tetrasodium 3-hydroxy-2,2'-iminodisuccinate, also referred to herein as sodium iminodisuccinate.

The preservative formulations disclosed herein are formulated to effectively replace conventional preservatives, to reduce the risk of toxicity and skin disorders (irritation, allergy) and to be safe to the environment.

The preservative chemical formulations disclosed herein are designed to be incorporated into skin care and hygiene products in a concentration range from about 0.1 to about 10 wt./wt. % of the formulations, and preferably from about 1 to about 3% wt./wt.

The preservative chemical formulations disclosed herein may be incorporated into surfactant-containing hygiene products or emulsions, gels and lotions for skin care purposes having potential antimicrobial activity, in a concentration range from 0.1 to 80 wt./wt. % of the finished products.

The final pH of the preserved formulations is preferably from about pH 3 to about 9, more preferably from about pH 4 to about pH 6, such a pH range taking the pKa of the acid into account.

Mode of Operation

Studies by the inventors using certain preferred constituents have been performed. The action of these preferred constituents and their mode of operation are discussed below, however it will be understood by those skilled in the art that the present invention is not to be limited by any theory. Studies by the inventors have shown that the preservative chemical formulations disclosed herein are able to inhibit the growth of Gram negative bacteria, Gram positive bacteria, yeasts and molds, all potential contaminants of water-based cosmetic and pharmaceutical products. While not meaning to be limited by any theory, the inventors believe that the mode of action on bacteria by the present formulations is mainly based on the inhibition of energy releasing biochemical reactions. On yeast and molds, the formulations are believed to disrupt the cell-wall. All involved ingredients are chosen to synergistically act on various cell-targets (metabolism, cell-wall, cell-membrane, cytoplasma, DNA, etc.) through chemical and physical modes of action.

In order to check the efficacy and effectiveness of the present formulations, a selected blend (sodium iminodisuccinate 5.50%, maleic acid 13.50%, phenyl hexanol 27.00% and ammonium sulphate 54.00%) was challenge-tested against four test-microorganisms, at final concentration of 3.00% in water, and according to the Pharmacopoeia ($V^{th}$ edition—2005) test-method. The following table shows the obtained results (expressed in terms of logarithm reductions). The blend passed the criteria for all test-microorganisms.

| Test-microorganisms | Pharmacopoeia $V^{th}$ Edition - 2005 (criteria) | Test-results |
|---|---|---|
| S. aureus | Day 2 ≥ 2 log | >4 log |
| ATCC 6538 | Day 7 ≥ 3 log | >4 log |
|  | Day 28 = no increase in count | >4 log |
| P. aeruginosa | Day 2 ≥ 2 log | >4 log |
| ATCC 9027 | Day 7 ≥ 3 log | >4 log |
|  | Day 28 = no increase in count | >4 log |
| C. albicans | Day 14 ≥ 2 log | >4 log |
| ATCC 10231 | Day 28 = no increase in count | >4 log |
| A. niger | Day 14 ≥ 2 log | 2.90 log |
| ATCC 16404 | Day 28 = no increase in count | 3.00 log |

Another test was conducted to determine the Minimum Inhibitory Concentration (from 1 to 4% w/w) of the same blend. The same test-microorganisms from the original ATCC cultures were grown and maintained in the laboratory according to the AFNOR EN12353 standard method.

Time and temperature of incubation were:
  24 h at 36±1° C. for bacteria
  48 h at 30±1° C. for yeasts and molds
Culture media were:
  TSA (Tryptic Soy Agar) for bacteria Sabouraud agar without chloramphenicol for yeasts and molds The following table shows the obtained results (expressed in terms of number of Unit Forming Colonies—UFC). In the test conditions, the blend may be considered to be bacteriostatic and fungistatic at 1% w/w for all test-microorganisms.

| Test-microorganisms | Initial count | UFC | | | |
|---|---|---|---|---|---|
| | | at 1% | at 2% | at 3% | at 4% |
| S. aureus ATCC 6538 | $1.4 \times 10^5$ | <1 | <1 | <1 | <1 |
| P. aeruginosa ATCC 9027 | $2.0 \times 10^5$ | <1 | <1 | <1 | <1 |
| C. albicans ATCC 10231 | $2.3 \times 10^5$ | <1 | <1 | <1 | <1 |
| A. niger ATCC 16404 | $1.1 \times 10^5$ | $7.9 \times 10^3$ | $4.8 \times 10^3$ | $1.3 \times 10^3$ | $1.6 \times 10^3$ |

Carboxylic Acid (Maleic Acid)

Micro-organisms produce enzymes in order to degrade proteins, lipids and carbohydrates from their immediate environment and absorb the vital smaller molecules as sources of carbon and energy. The necessity for a close and fast-acting fit between enzyme and substrate explains the phenomenon of competitive inhibition.

The term metabolism refers to the sum of the biochemical reactions required for energy generation and the use of energy to synthesize cell material from small molecules in the environment. Metabolism has an energy-generating component referred to as "catabolism", and an energy-consuming component referred to as "anabolism". Catabolic reactions produce energy as ATP (Adenosine 5'-TriPhosphate) which can be utilized in anabolic reactions to build cell material. The relationship between catabolism and anabolism is illustrated in FIG. 1.

During catabolism, useful energy is temporarily conserved in the "high energy phosphoric bond" of ATP. No matter what form of energy a cell uses as its primary source, the energy is ultimately transformed and conserved as ATP—the universal currency of energy exchange in biological systems.

When energy is required during anabolism, it may be spent as the high energy bond of ATP which has a value of about 8 kcal per mole. Hence, the conversion of ADP to ATP requires 8 kcal of energy, and the hydrolysis of ATP to ADP releases 8 kcal.

ATP acts as a coenzyme in energetic coupling reactions wherein one or both of the terminal phosphate groups is removed from the ATP molecule with the bond energy being used to transfer part of the ATP molecule to another molecule to activate its role in metabolism.

For example, Glucose+ATP→Glucose-P+ADP; or

Amino Acid+ATP→AMP-Amino Acid+Pyrophosphate

Figure 2:
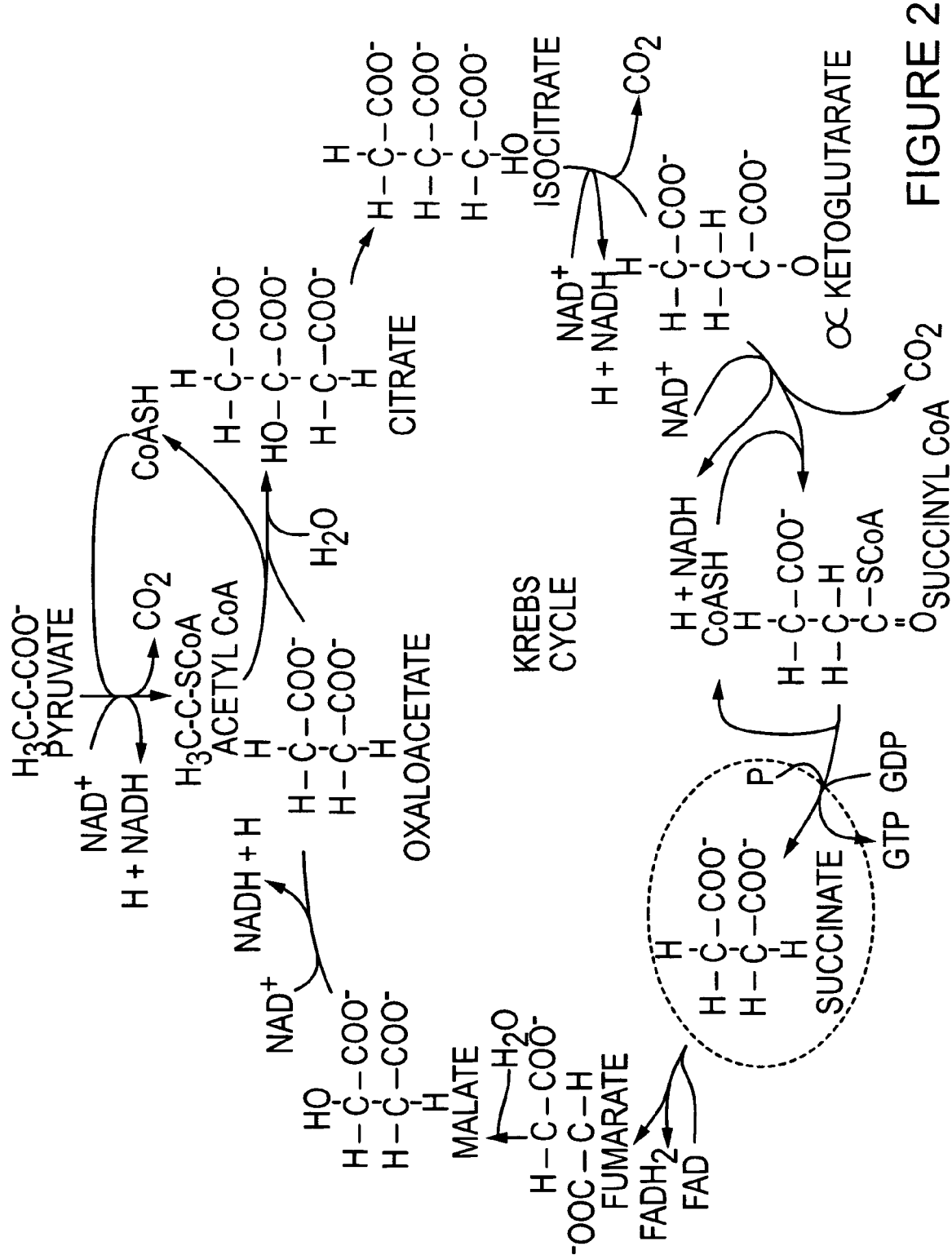
FIG. 2 illustrates the Krebbs cycle.

One of the enzymes needed for the release of energy within the cell is succinic dehydrogenase. It acts as a carrier for hydrogen removed in the aerobic oxidation of carbohydrate in the Krebs cycle (see FIG. 2).

The purpose of the Krebs (or tricarboxylic acid) cycle is to complete the biochemical breakdown of food to produce energy-rich molecules, which the organism can use to fuel work. Acetyl coenzyme A (acetyl CoA), produced by the breakdown of sugars, fatty acids, and some amino acids, reacts with oxaloacetic acid to produce citric acid, which is then converted in a series of enzyme-catalysed steps back to oxaloacetic acid. In the process, molecules of carbon dioxide and water are given off, and the precursors of the energy-rich molecules ATP are formed.

The final part of the chain of biochemical reactions by which organisms break down food using oxygen to release energy (respiration) which takes place within structures called mitochondria in the body's cells, and breaks down food molecules in series of small steps, producing energy-rich molecules of ATP.

Figure 3:
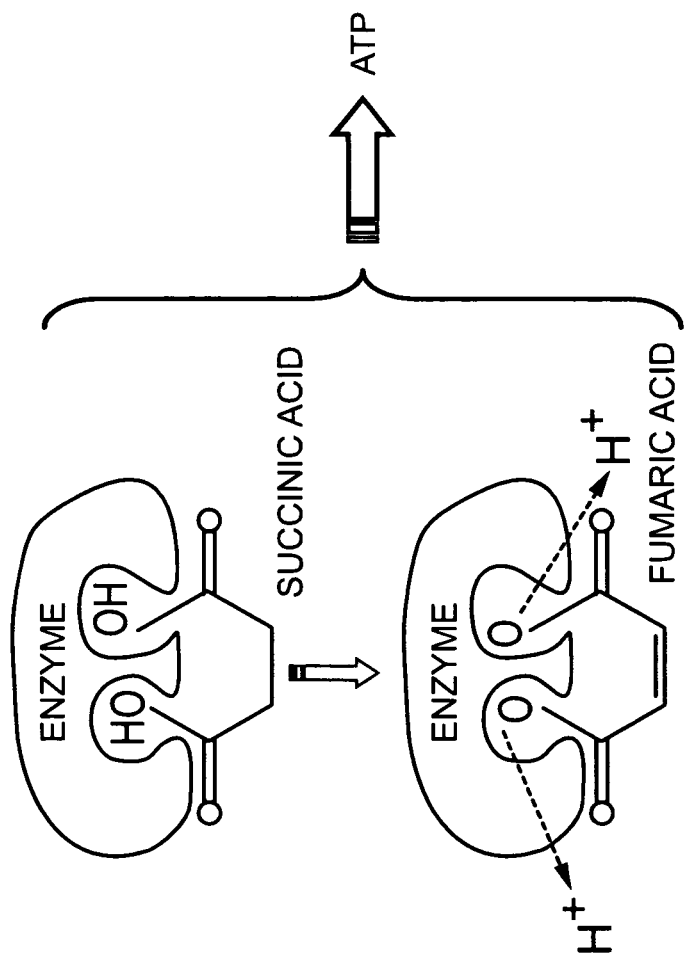
FIG. 3 is a diagrammatic representation showing the production of Adenosine TriPhosphate (ATP) which occurs within the bacterial cells and within mitochondria in the body's cells, in which the bacterial enzyme succinic dehydrogenase catalyzes the oxidation (by the removal of two hydrogen atoms) of succinic acid into fumaric acid, this process produces energy in the form of energy-rich molecules of AdenosineTriPhosphate (ATP)

Referring to FIG. 3, the bacterial enzyme succinic dehydrogenase is required to catalyze the oxidation (by the removal of two hydrogen atoms) of succinic acid into fumaric acid. This process produces energy under the form of AdenosineTriPhosphate (ATP).

Figure 4:
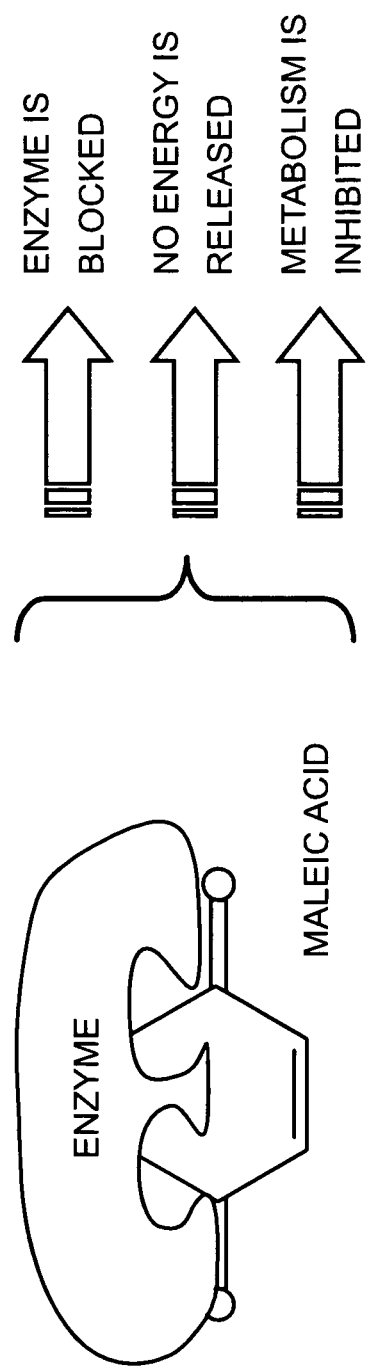
FIG. 4 is a diagrammatic representation showing the action of a constituent of a preservative formulation, maleic acid, in blocking the active site of an enzyme.

Referring to FIG. 4, the inventors believe it is possible to block the active site of the enzyme by using a molecule which chemically looks like the substrate. The structure of maleic acid for instance allows it to bind to the same site on the enzyme. The inhibition is called competitive because if the ratio of succinic/maleic acid in the mixture increased, the rate of catalysis is gradually restored.

Sodium Iminodisuccinaate

Sodium Iminodisuccinaate is a safe and biodegradable cosmetic chelating agent. Bacteria require metal ions to satisfy the specific requirements of metal-enzyme and cell-wall structural components. Chelators are able to increase the permeability of the bacterial cell wall by sequestering the necessary metals ($Fe^{2+}$ in particular). They also can capture the metal ions ($Mg^{2+}$ in particular) acting as cofactors for the DNA synthesis and in the LipoPolySaccharide's cohesion. Chelators are known to improve the antimicrobial activity of biocidal molecules.

Phenyl Hexanol

Aromatic alcohols are used in a great number of alternative preservatives. Phenyl ethanol is the most widely used but it has strong 'flowery' smell; a chemical structure analogue such as phenyl hexanol is a good alternative and has almost no smell.

Nerolidol

A natural sesquiterpene with bactericidal and fungicidal properties. A study consisting of evaluating the antibacterial effects of three terpene-alcohols (farnesol, nerolidol and plaunotol) on Staphylococcus aureus, focusing on the leakage of K+ ions and toxicity over time, suggested that the terpene alcohols may act on cell membranes. The antibacterial activity reflected the initial rate of leakage of K+ ions, suggesting that damage to cell membranes might be one of the major modes of action of these terpene alcohols. The results also demonstrated that the initial rate of leakage and the amount of leaked K+ ions are useful as indices of the antibacterial activities of hydrophobic compounds, see Yoshihiro Inouea, Akiko Shiraishia, Toshiko Hadaa, Kazuma Hirosea, Hajime Hamashimaa, Jingoro Shimada; "The antibacterial effects of terpene alcohols on Staphylococcus aureus and their mode of action", FEMS microbiology letters (FEMS microbial. lett.) 2004, vol. 237, no 2, pp. 325-331.

In another study, sesquiterpenoids nerolidol, farnesol, bisabolol, and apritone were investigated for their abilities to enhance bacterial permeability and susceptibility to exogenous antimicrobial compounds. Initially, it was observed by flow cytometry that these sesquiterpenoids promoted the intracellular accumulation of the membrane-impermeant nucleic acid stain ethidium bromide by live cells of Lactobacillus fermentum, suggesting that enhanced permeability resulted from disruption of the cytoplasmic membrane. The ability of these sesquiterpenoids to increase bacterial susceptibility to a number of clinically important antibiotics was then investigated. In disk diffusion assays, treatment with low concentrations (0.5 to 2 mM) of nerolidol, bisabolol, or apritone enhanced the susceptibility of *Staphylococcus aureus* to ciprofloxacin, clindamycin, erythromycin, gentamicin, tetracycline, and vancomycin. Nerolidol and farnesol also sensitized *Escherichia coli* to polymyxin B, see Byron F. Brehm-Stecher1 and Eric A. Johnson Sensitization of *S. aureus* and *E. coli* to Antibiotics by the Sesquiterpenoids Nerolidol, Farnesol, Bisabolol, and Apritone Antimicrob Agents Chemother. 2003 October; 47(10): 3357-3360.

Another study undertaken to elucidate the antifungal activities of eugenol and nerolidol isolated from Japanese cypress oil in a guinea pig model infected by *Microsporum gypseum* (*M. gypseum*). A minimal inhibitory concentration (MIC), skin lesion scoring, hair culture and histopathologic examination of skin tissues were performed to evaluate the antifungal effect of these oils. The MICs of eugenol, nerolidol and econazole (positive control) were 0.01-0.03% and 0.5-2% and 4-16 µg/ml, respectively. Based on these MICs, eugenol and nerolidol were adjusted to 10% concentration with a base of Vaseline® petroleum jelly and were applied topically to the skin lesion infected with *M. gypseum* daily for 3 weeks. Both eugenol and nerolidol were clinically effective at improving the lesion during the first week of application, as determined by skin lesion scoring. Nerolidol improved the skin lesions infected by *M. gypseum*, but eugenol did not, as determined in the hair culture test. Histopathologic examination revealed that the eugenol- and nerolidol-treated groups had a lower degree of hyperkeratosis and inflammatory cell infiltration than the positive control. Taken together, these results suggest that eugenol and nerolidol could apply supplementary antifungal agents, see Sook-Jin Lee[1], Je-Ik Han[1], Geun-Shik Lee[2], Mi-Jin Park[3], In-Gyu Choi[3], Ki-Jeong Na[1] and Eui-Bae Jeung[2] Antifungal Effect of Eugenol and Nerolidol against *Microsporum gypseum* in a Guinea Pig Model, Biological & Pharmaceutical Bulletin, Vol. 30 (2007), No. 1 184.

Ammonium Sulphate

This salt has the potential to precipitate enzymes involved in the bacterial enzymes as well as those involved in the biosynthesis of fungal ergosterol (one of the major components of molds and yeasts membrane). In the present formulations, it is believed to contribute to the inhibition of bacterial and fungal growth.

The present invention will now be illustrated using the following non-limiting example formulations.

EXAMPLE 1

| Chemical Names (INCI) | % w/w |
| --- | --- |
| SODIUM IMINODISUCCINATE | 5.50 |
| MALEIC ACID | 13.50 |
| PHENYL HEXANOL | 27.00 |
| AMMONIUM SULFATE | 54.00 |

The formulation of example 1 is useful to be incorporated into cosmetic formulations in a range from about 1 to about 4% wt./wt. in finished products.

EXAMPLE 2

| Chemical Names (INCI) | % w/w |
| --- | --- |
| SODIUM IMINODISUCCINATE | 6.30 |
| MALEIC ACID | 15.60 |
| NEROLIDOL | 15.60 |
| AMMONIUM SULFATE | 62.50 |

EXAMPLE 3

| Chemical Names (INCI) | % w/w |
| --- | --- |
| SODIUM IMINODISUCCINATE | 4.80 |
| MALEIC ACID | 11.90 |
| PHENYL HEXANOL | 23.80 |
| NEROLIDOL | 11.90 |
| AMMONIUM SULFATE | 47.60 |

The above blends are preferably incorporated into skin care and hygiene products in a concentration range from 0.1 to 10 wt./wt. % of the finished products.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A preservative formulation for skin care and hygiene products, comprising constituents including:
    a) at least one organic carboxylic acid that is maleic acid present in a concentration from about 0.01 to about 30 wt./wt. % of the formulation;
    b) at least one alcohol that is a phenyl alcohol present in a concentration from about 0.01 to about 60 wt./wt. % of the formulation;
    c) ammonium sulphate present in a concentration from about 0.01 to about 80 wt./wt. % of the formulation; and
    d) at least one chelating agent that is a sodium salt of iminodisuccinic acid present in a concentration from about 0.01 to about 20 wt./wt. % of the formulation.

2. The formulation according to claim 1 wherein said at least one alcohol is phenyl hexanol.

3. The formulation according to claim 1 wherein said at least one chelating agent is tetrasodium 3-hydroxy-2,2'-iminodisuccinate.

4. The formulation according to claim 1 incorporated into a personal hygiene product to form a preserver personal hygiene product, said formulation being present in a concentration range from about 0.1 to about 10 wt./wt. % of the preserved personal hygiene product.

5. The preserved personal hygiene product according to claim 4 wherein said personal hygiene product contains surfactants.

6. The preserved personal hygiene product according to claim 4 wherein a final pH of the preserved personal hygiene product is in a range from about pH 3 to about pH 6.

7. The formulation according to claim 1 wherein said at least one alcohol is phenyl hexanol and wherein said at least one chelating agent is sodium iminidisuccinate.

8. The formulation according to claim 7 wherein said sodium iminodisuccinate is present in an amount of about 5.5% wt./wt., and wherein said maleic acid is present in an amount of about 13.5% wt./wt., and wherein said phenyl hexanol is present in an amount of about 27% wt./wt., and wherein said ammonium sulphate is present in an amount of about 54% wt./wt.

9. The formulation according to claim 1 wherein said at least one chelating agent is sodium iminodisuccinate.

10. The formulation according to claim 9 wherein said sodium iminodisuccinate is present in an amount of about 6.3% wt./wt., and wherein said maleic acid is present in an amount of about 15.6% wt./wt., and wherein said ammonium sulphate is present in an amount of about 62.5% wt./wt.

11. The formulation according to claim 7 wherein said sodium iminodisuccinate is present in an amount of about 4.8% wt./wt., and wherein said maleic acid is present in an amount of about 11.9% wt./wt., and wherein said phenyl hexanol is present in an amount of about 23.8% wt./wt., and wherein said ammonium sulphate is present in an amount of about 47.6% wt./wt.

* * * * *